United States Patent [19]

Roehl

[11] Patent Number: 4,561,997

[45] Date of Patent: Dec. 31, 1985

[54] PROCESS FOR THE PREPARATION OF AIR-REFRESHING GELS AS WELL AS THE OBTAINED GELS

[75] Inventor: Ernst-Ludwig Roehl, Naarden, Netherlands

[73] Assignee: Naarden International N.V., Netherlands

[21] Appl. No.: 523,750

[22] Filed: Aug. 16, 1983

[30] Foreign Application Priority Data

Aug. 20, 1982 [NL] Netherlands ............... 8203275

[51] Int. Cl.$^4$ .............................................. A01K 7/46
[52] U.S. Cl. ................................................. 252/522 A
[58] Field of Search .................................... 252/522 A

[56] References Cited

U.S. PATENT DOCUMENTS

| | | | |
|---|---|---|---|
| 2,871,526 | 2/1959 | Bulloff | 21/108 |
| 3,446,893 | 5/1969 | Hanford et al. | 424/76 |
| 3,661,838 | 5/1972 | Enomoto | 260/41 A |
| 3,767,787 | 10/1973 | Segal | 424/76 |
| 3,969,280 | 7/1976 | Sayce et al. | 252/522 R |
| 4,178,264 | 12/1979 | Streit et al. | 252/316 |

FOREIGN PATENT DOCUMENTS

| | | |
|---|---|---|
| 2293976 | 7/1976 | France . |
| 7309675 | 1/1974 | Netherlands . |
| 7309629 | 1/1974 | Netherlands . |
| 7502596 | 9/1975 | Netherlands . |
| 7602254 | 9/1976 | Netherlands . |
| 7611041 | 4/1977 | Netherlands . |
| 7612909 | 5/1977 | Netherlands . |
| 1401550 | 7/1975 | United Kingdom . |
| 1430207 | 3/1976 | United Kingdom . |
| 1432163 | 4/1976 | United Kingdom . |
| 1438098 | 6/1976 | United Kingdom . |
| 1503897 | 3/1978 | United Kingdom . |
| 1515630 | 6/1978 | United Kingdom . |

OTHER PUBLICATIONS

Derwent Abstract of Japanese Application Ser. No. 54,110,990, 8/30/79.
Derwent Abstract of Japanese Application 53/3088334, 8/3/78.
Derwent Abstract of Japanese Application 52/136,893, 11/15/77.
Derwent Abstract of Japanese Application 52/070,035, 6/10/77.

*Primary Examiner*—Anton H. Sutto
*Attorney, Agent, or Firm*—Brumbaugh, Graves, Donohue & Raymond

[57] ABSTRACT

Aqueous air-freshener gels having an increased content of perfume are prepared by homogeneously mixing the perfume with one or more solid inorganic carriers selected from the group consisting of magnesium, oxide powder, active carbon, zeolites and absorption agents based on silica and then combining the homogeneous mixture obtained in this way with an aqueous gel or the gel forming components. In the case of absorption agents based on silica or zeolites the further use of a non-ionogenic emulsifier is required.

5 Claims, No Drawings

PROCESS FOR THE PREPARATION OF AIR-REFRESHING GELS AS WELL AS THE OBTAINED GELS

The invention relates to a process for the preparation of air-freshener gels.

Air-freshener gels are popular consumer products. They consist of a perfume containing carrier material, from which the perfume evaporates slowly and thus gives a pleasant smell to the atmosphere. The life time and the amount of perfume emitted per time unit are determined mainly by the amount of perfume in the air-freshener. In many known types of air-fresheners gelled water is used as carrier material. Because perfumes are generally not or hardly soluble in water they should be dispersed therein as homogeneously as possible. Furthermore gelled organic solvents like monohydric or polyhydric alcohols or glycol ethers are used as carrier materials. However, water has the advantage of being cheap and toxicologically unsuspected.

Aqueous gels may be prepared in many ways known as such using as gelling agent e.g.: vegetable gums like carragheenin, agar agar, alginates, pectine, guar gum, tragacanth, karaya gun, xanthan etc. and further for instance gelatin as well as starch and cellulose derivatives. In some cases the gel strength can be increased by the addition of salts of bivalent or polyvalent metals like Ca, Mg, Al or Cr. Furthermore synthetic polymers like polyvinyl alcohol may be used as gelling agent.

Such aqueous gels have the disadvantage that they only may contain a limited amount of perfume. In the literature mostly a maximum perfume content of about 10% is mentioned but in practice it appears that a perfume content of more than about 6% strongly reduces the gel strength and/or causes syneresis whereby the perfume leaves the gel as a liquid. Aqueous perfume gels are described for instance in the published Japanese patent applications No. 54,110,990 (gelling agent: carragheenin and sodium stearate, perfume content up to 6%); No. 53,088,334 (gelling agent: bacterial polysaccharide, 1-10% of perfume); and No. 52,136,893 (gelling agent: carragheenin and polyvinyl alcohol, 2-4% of perfume), and in the French patent application No. 2,293,976 (gelling agent: carboxymethyl cellulose/Al-salt, 5% of perfume).

Furthermore Dutch patent application No. 76,11041 also discloses the use of carboxymethyl cellulose and salts of trivalent metals as gelling agents in aqueous perfume gels. Although it is mentioned in the specification that these gels may contain up to 20% of perfume the examples only illustrate a perfume content of 4%. Likewise Dutch patent application No. 76,02254 discloses similar aqueous perfume gels which would contain up to 10% of perfume whereas in the examples only gels are illustrated containing up to 2.5% of perfume. Dutch patent application No. 75,02596 describes aqueous gels based on mixtures of carragheenin and locust bean gum which according to the specification may also contain up to 10% of perfume, however, from the examples it appears that no more than 3.3% of perfume is used.

Dutch patent application No. 76,12909 discloses gels based on amylose as gelling agent. In the specification it is indicated that the perfume content of these gels is 0.25-30% perferably 0.5-5%. It is true that one of the examples discloses a gel containing 30% of perfume, however, for that result a content of 10% of pure (and therefore expensive) amylose is required. When starch containing 70% of amylose is used no stable gel can be produced yet with even 10% of perfume. Furthermore these gels have the disadvantage that for the preparation of the necessary amylose-solution high temperatures (up to 170° C.) and pressures (up to 7 atm) are required and therefore relatively complicated equipment.

In some of the above mentioned patent applications it is mentioned that preferably the perfume is used together with an amount of emulsifier for promoting the homogeneous distribution of the perfume in the aqueous phase. In Japanese patent application No. 52,070,035 it is stated that aqueous gels cannot contain more than 2-3% of perfume unless a non-ionogenic emulsifier is added in a amount of 0.5-1.5 times the amount of perfume, in which case the perfume content of the gel may rise to 10%. Anyway the amount of perfume which can be distributed homogeneously in an aqueous gel highly depends on the solubility of the perfume in water and thus on the type of the components composing the perfume.

The phrase "perfume" is used to mean a mixture of organic compounds like aldehydes, ketones, nitriles, esters, carboxylic acids, alcohols, ethers etc. which may also contain natural products like essential oils, resinoids, balsams, concrètes etc. This mixture is meant to emit a desired smell. In many cases a perfume contains a mostly small amount of a solvent or diluent usual in perfumery, for instance because one or more of the components used in the composition are only available or manageable in solution.

The purpose of the invention is to provide aqueous air-freshener gels having an increased perfume content and for that reason a longer lifetime and/or a higher perfume emission per time unit. The phrase "increased perfume content" means in this respect a content of at least 5% and preferably more than 10% based on the total weight of the gel.

It has been found that such air-freshener gels can be prepared by previously mixing the perfume with specific solid inorganic carrier materials and then introducing this mixture, which hereinafter will be called "premix" in an aqueous gel. As specific solid inorganic carrier materials are mentioned: magnesium oxide powder, active carbon, zeolites and absorption agents based on silicon dioxide (silica) like many kinds of silica gel, bentonite and especially hydrophobic or non-hydrophobic pyrogenic silica. Furthermore mixtures consisting of solid materials can be used as far as they mainly consist of one or more of the above mentioned types of carrier materials.

In Dutch patent application No. 76,11041 it is mentioned that for the preparation of the aqueous gels described therein considerable amounts of fillers can be used such as graphite, carbon, carbon black, silicates and several kinds of silica. However, no special process for the preparation of aqueous gels is indicated therein nor it is mentioned therein that these fillers should meet specific requirements. Furthermore it is not indicated either that by addition of these fillers the gels could contain more perfume. This last aspect is even improbable because the addition of fillers will decrease the amount of aqueous perfume dispersion per weight unit of gel and for that reason the perfume content. Therefore the mentioned prolongation of the perfume emission should be ascribed to retarded evaporation. However, this has the disadvantage that more gel or a larger evaporating surface is required for obtaining sufficient perfume emission per time unit.

Surprisingly the process according to the invention whereby the perfume is absorbed previously on one or more of the above mentioned inorganic carrier materials offers the opportunity to introduce much larger amounts of perfume in aqueous gels than was usual up to now.

The aqueous gels according to the invention can be prepared by using gelling agents known and usual for aqueous gels as for instance described in the already mentioned patent specifications and patent applications and the literature cited therein. As already mentioned before, very suitable gelling agents are for instance agar agar, carragheenin and modified cellulose like methyl cellulose, hydroxyethyl cellulose and carboxymethyl cellulose. Some gelling agents may advantageously be combined with a salt of a polyvalent metal as crosslinking agent. Part of the water used for preparing the gel can optionally be replaced by water miscible organic solvents like monohydric or polyhydric alcohols for instance ethanol, isopropanol, ethylene glycol etc. as far as these solvents do not affect the activity of the gelling agent. For economic reasons this replacement is generally not recommended because organic solvents are more expensive than water.

The amount of perfume which is present in the air-freshener gel according to the invention is determined, on the one hand, by the amount of perfume in the premix and, on the other hand, by the amount of premix in the gel. This last amount is not subjected to any fundamental restriction but in practice is restricted by the fact that on preparing the gel mixture the viscosity increases with an increasing amount of premix. Therefore the maximum amount of premix to be used is determined by the demands made by the processing of the gel mixture during and after the preparation and the equipment which is available for the preparation. When the demand is made that the mixture directly after the preparation should be so liquid that it simply can be poured into molds, the maximum amount of the premix in the gel is about 35%. However, when for the preparation heavy duty stirring equipment is used and the gel packings are filled by means of equipment and operations under pressure, considerably higher premix contents are achievable.

The maximum perfume content in the premix is determined by the requirement that the premix should be a solid mixture which optionally may be lumpy and feeling moist. To meet this requirement the minimum amount of solid carrier material in the premix depends on the type of carrier material. It varies from about 60% for bentonite to about 10% for some highly porous kinds of pyrogenic silica. For active carbon and magnesium oxide the minimum contents are about 40% and about 30% respectively.

When using active carbon or magnesium oxide as solid carrier material the addition of emulsifiers is not recommended because this affects the stability of the gels according to the invention. On the contrary, by using a zeolite or a carrier material based on silica it is necessary to previously mix the perfume homogeneously with a non-ionogenic emulsifier in an amount of 5–200%, calculated on the weight of the perfume. Preferably emulsifiers having a HLB-value of 9 or more are used such as esters of fatty acids and polyethylene glycols and condensation products of alkylphenols or fatty alcohols with ethylene oxide.

An air-freshener gel preparable with simple means and containing at most 35% of premix will therefore will regard to the above mentioned requirements generally have a composition mentioned in the following table:

|  |  | preferably |
|---|---|---|
| inorganic carrier material | 0.5–30% | 1.5–25% |
| perfume | 5–30% | 10–25% |
| emulsifier (only in the case of silica or zeolite) | 0.5–20% | 1–5% |
| water (optionally partly replaced by a water miscible organic solvent) | 50–93% maximum | 87% |
| gelling agent | 0.5–10% |  |
| polyvalent metal salt | 0–5% |  |
| preservative | 0–1% |  |
| dye | 0.1% |  |

The gel is prepared according to methods known per se for such products, except that the process of the invention differs from these methods in that the perfume is previously mixed with the solid carrier material according to the invention into a homogeneous mixture called premix. If the carrier material is a zeolite or a carrier material based on silica the perfume is stirred homogeneously with a non-ionogenic emulsifier before said mixing stage. The ready premix is then mixed with the water, the gelling agent and optionally the metal salt, the preservative and the dye. Preferably water and gelling agent are mixed previously and then the premix is added as soon as possible. Some gel mixtures are preferably prepared at elevated temperatures and then at these temperatures poured into molds. After cooling to room temperature the gel mixture solidifies. However, other gel types can be prepared at room temperature and remain liquid for a sufficiently long time to be poured into molds. All these and similar methods can be used for the preparation of the gels according to the invention. An example of a perfume that can be used in the gels according to the invention was prepared according to the following recipe:

| 300 | parts by weight of bornyl acetate |
| 200 | parts by weight of orange oil Florida |
| 140 | parts by weight of β-phenylethanol |
| 100 | parts by weight of geraniol |
| 100 | parts by weight of α-pentyl-cinnamaldehyde |
| 75 | parts by weight of benzyl acetate |
| 50 | parts by weight of dihydromyrcenol |
| 30 | parts by weight of 2.4-dimethyl-3-cyclohexene-carbaldehyde |
| 5 | parts by weight of decanal |
| 1000 | parts by weight |

The examples are only intended as illustration of the process according to the invention. The invention is not restricted thereto:

EXAMPLE I 15 g of perfume according to the above mentioned recipe and 2 g of Arlypon NP-14[1] were mixed and stirred homogeneously. Then 5 g of Aerosil[2] was added and the product was mixed until an almost dry homogeneous powder was obtained. The so prepared 22 g of premix was homogeneously dispersed in 20 g of water while heating to about 75° C. 2.3 g Carragheenin, 0.2 g of chloroacetamide and 0.5 g of CaCl$_2$.2H$_2$O were dissolved in 55 g of water while heating to about 75° C. This somewhat viscous solution was added to the above described dispersion of premix in water. The total mixture was stirred completely homogeneous and poured into molds while warm. After cooling to room temperature firm and stable air freshener gels were obtained having a perfume content of 15%.

[1] Arlypon NP-14 is a non-ionogenic emulsifier, marketed by Chemische Werke Grünau, Illertissen, West-Germany.
[2] Aerosil is a pyrogenix silica, marketed by Degussa, Hanau, West-Germany.

EXAMPLE II

According to the method described in Example I 31.5 g of a somewhat moist feeling but solid premix was obtained from 25 g of the above mentioned perfume, 2.5 g of Arlypon NP-14 and 4 g of Aerosil. 45 g of aqueous dispersion was obtained by addition of water. 2.3 g of carragheenin, 2 g of chloroacetamide and 0.5 g of $CaCl_2.2H_2O$ were dissolved at 75° C. in 52 g of water. The warm premix dispersion and carragheenin solution were mixed, stirred homogeneous and discharged into molds. After cooling to room temperature firm and stable air-freshener gels were obtained having a perfume content of 25%.

EXAMPLE III

According to Example I a premix was prepared from 20 g of perfume, 2 g of Arlypon NP-14 and 5 g of Aerosil. A gel solution was prepared by dissolving 4 g of agar agar in 62.8 g of boiling water. After cooling to about 70° C. 5 g of ethanol, 1 g of propylene glycol and 0.2 g of a 35% formaldehyde solution were added. Finally the above described premix was added, the mixture stirred homogeneous and poured into molds while warm. The air-freshener gels obtained after cooling had a perfume content of 20%.

EXAMPLE IV

A premix was prepared by thoroughly mixing of 19 g of perfume with 11 g of magnesium oxide powder. A gel solution was prepared by dissolving 0.5 g of $CaCl_2.2H_2O$, 0.2 g of a 10% solution of 5-bromo-5-nitro-1.3-dioxane in propylene glycol (preservative) and 2.6 g of carragheenin in 66.7 g of water at 85° C. After the complete mixture was stirred homogeneous, the above described premix was added, the mixture was stirred homogeneous again and poured into molds while warm. The air-freshener gels obtained after cooling had a perfume content of 19%.

EXAMPLE V

The process of Example IV was repeated but now with a premix consisting of 15 g of perfume and 15 g of active carbon. The air-freshener gels obtained had a perfume content of 15%.

I claim:

1. A process for the preparation of aqueous air-freshener gels containing a perfume characterized by homogeneously mixing the perfume with one or more solid inorganic carrier materials selected from the group consisting of magnesium oxide powder, active carbon, zeolites and absorption agents based on silica and then combining the homogeneous mixture obtained in this way with an aqueous gel or the gel forming components, said perfume having been previously mixed homogeneously with a non-ionogenic emulsifier in an amount of 5–200% calculated on the weight of the perfume, when zeolites or absorption agents based on silica are used.

2. The process according to claim 1, characterized by using silica gel, bentonite, and/or hydrophobic or non-hydrophobic pyrogenic silica as absorption agents based on silica.

3. The process according to claim 1, characterized by using an emulsifier having a HLB-value of at least 9 as the non-ionogenic emulsifier.

4. The process according to claim 1, characterized by preparing an air-freshener gel consisting of:

| | |
|---|---|
| inorganic carrier material as indicated in claim 1 | 0.5–30% by weight |
| perfume | 5–30% by weight |
| emulsifier (only in the case of carriers based on silica or zeolites) | 0.5–20% by weight |
| water (optionally partly replaced by a water miscible organic solvent) | 50–93% by weight |
| gelling agent | 0.5–10% by weight |
| polyvalent metal salt | 0–5% by weight |
| preservative | 0–1% by weight |
| dye | 0.1% by weight |

5. Air-freshener gels obtained by applying the process according to claim 1.

* * * * *